United States Patent [19]

Burg et al.

[11] Patent Number: 4,575,500

[45] Date of Patent: Mar. 11, 1986

[54] ANTIFUNGAL SUBSTANCES AND PROCESS FOR THEIR PRODUCTION

[75] Inventors: Richard W. Burg, Murray Hill; Lucille J. Cole, Warren, both of N.J.; Sebastian Hernandez, Madrid, Spain

[73] Assignee: Merck & Co., Inc., Rahway, N.J.

[21] Appl. No.: 593,448

[22] Filed: Mar. 26, 1984

[51] Int. Cl.$^4$ .......................... A01N 57/12; C07F 9/09
[52] U.S. Cl. .................................. 514/121; 514/125; 558/169; 435/128; 435/898

[58] Field of Search ................ 260/924, 946; 514/124, 514/121

Primary Examiner—Anton H. Sutto
Attorney, Agent, or Firm—David L. Rose; Michael C. Sudol, Jr.; Mario A. Monaco

[57] ABSTRACT

There is disclosed a series of macrolides isolated from the fermentation broth of a microorganism identified as MA-5000 which morphological analysis reveals to be a strain of *Streptomyces hygroscopicus*. The compound's structure is presented based upon analytical studies. The compound has antifungal activity.

7 Claims, 4 Drawing Figures

ANTIFUNGAL SUBSTANCES AND PROCESS FOR THEIR PRODUCTION

SUMMARY OF THE INVENTION

This invention is concerned with novel organic chemical compounds. In particular, it is concerned with phosphate esters which are produced by the fermentation of a nutrient medium with a strain of the microorganism *Streptomyces hygroscopicus* MA-5000. Thus, it is an object of this invention to provide for such novel compound, and a method for preparing such product microbiologically. It is a further object of this invention to provide for the recovery and purification of such compounds from the fermentation broth. These substances have antifungal activity, and it is, thus, an additional object of this invention to provide for novel antifungal compositions containing the disclosed compounds. Further objects of this invention will become apparent from the following description of this invention.

DESCRIPTION OF THE INVENTION

In accordance with this invention, a series of novel substances is described, which are prepared by growing under controlled conditions, a previously undescribed strain of a microorganism. A single novel compound is produced by *Streptomyces hygroscopicus* MA-5000. The compound is obtained by fermentation and recovered in substantially pure form as described herein.

Based on taxonomic studies, the microorganism capable of producing these compounds is of a new strain of the microorganism *Streptomyces hygroscopicus*. One such culture, isolated from soil, is designated MA-5000 in the culture collection of Merck & Co., Inc., Rahway, N.J. A sample of this culture, capable of producing the herein described compound, has been deposited, without restriction as to availability, in the permanent culture collection of the American Type Culture Collection at 12301 Parklawn Drive, Rockville, Md. 20852, and has been assigned the accession number ATCC 39476.

The morphological and cultural characteristics of *Streptomyces hygroscopicus* MA-5000 are set forth below:

CULTURAL CHARACTERISTIC OF: *Streptomyces hygroscopicus* MA-5000-ATCC 39476 (V-vegetative growth; A=aerial mycelium; SP=soluble pigment)

Morphology: Sporophores form compact spirals along aerial hyphae. As culture ages, spore chains coalesce to form dark moist areas. Spore surface by electron microscope (TEM) shows a smooth surface on some spores and a rough to warty surface on others.

Oatmeal agar (ISP Medium 3)

V: Reverse—brown edged with dark brown
A: Dark gray mixed with white and light gray, becoming black and moist with age.
SP: Lt. grayish-brown.

Czapek Dox agar (sucrose nitrate agar)

V: Reverse—dark brown
A: moderate, grayish white
SP: Lt. brown

Egg albumin agar

V: Flat, spreading, grayish-brown
A: Light gray mixed with white and edged with dark gray, some areas becoming moist and black.
SP: Light brown Glycerol asparagine agar (ISP Medium 5)

V: Reverse—dark yellow brown
A: Light gray mixed with white and yellowish white. Droplets of golden yellow exudate are present.
SP: Lt. tan Inorganic salts-starch agar (ISP Medium 4)

V: Reverse—light gray-brown edged with dark gray
A: Dark gray mixed with light gray and white, becoming black and moist.
SP: Light grayish-brown Yeast extract-malt extract agar (ISP Medium 2)

V: Reverse—dark yellow brown
A: Dark gray becoming black and moist with age. Droplets of golden yellow exudate also present.
SP: Light brown Peptone-iron-yeast extract agar V: tan
A: sparse, whitish
SP: None
Melanin: negative Nutrient tyrosin agar V: Rev.—brown
A: Moderate, light gray
SP: Light brown Tyrosine Agar (ISP Medium 7)

V: Reverse—dark brown
A: Gray edged with dark gray; droplets of golden yellow exudate present
SP: Light brown Carbon utilization Pridham-Gottlieb basal medium+1% carbon source;
+ =growth; ± =growth poor or questionable;
− =no growth as compared to negative control (no carbon source)

| | |
|---|---|
| Glucose | + |
| Arabinose | ± |
| Cellulose | − |
| Fructose | + |
| Inositol | + |
| Lactose | ± |
| Maltose | + |
| Mannitol | + |
| Mannose | + |
| Raffinose | ± |
| Rhamnose | ± |
| Sucrose | + |
| Xylose | ± |
| Temperature range | (Yeast extract-dextrose + salts agar) |
| 26° C. - Good vegetative growth and sporulation | |
| 37° C. - Good vegetative growth scant aerial mycelia | |
| 50° C. - No growth | |

Oxygen requirement (Stab culture in yeast extract-dextrose+salts agar)

Aerobic

All readings taken after three weeks at 28° C. unless noted otherwise. pH of all media approximately neutral (6.8–7.2)

A careful comparison of the foregoing data with published descriptions, including Bergey's *Manual of Determinative Bacteriology* 8th ed (1974); Waksman, *The Actinomycetes* Vol. II (1961); International Journal of Systematic Bacteriology 18, 68–189, 279–392 (1968); 19, 391–512 (1969); 22, 265–394 (1972); shows a close correlation between the description of a bacterium identified as *Streptomyces hygroscopicus* and the morphological and cultural characteristics of MA-5285. It is therefore determined that MA-5285 is a new strain of the known species *Streptomyces hygroscopicus*.

The above description is illustrative of a strain of *Streptomyces hygroscopicus* MA-5000 which can be employed in the production of the instant compound. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

The instant compound is produced during the aerobic fermentation of suitable aqueous nutrient media under conditions described hereinafter, with a producing strain of *Streptomyces hygroscopicus* MA-5000. Aqueous media such as those used for the production of many antibiotic substances are suitable for use in this process for the production of this macrocyclic compound.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, caesin hydrolysates, yeast extracts, corn steep liquors, distillers solubles, cottonseed meal, meat extract and the like, are readily assimilable by *Streptomyces hygroscopicus* MA-5000 in the production of the instant compound. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like. For the best production of the instant compound, the addition of calcium carbonate to the production medium is most preferred.

It should be noted that the media described hereinbelow and in the Examples are merely illustrative of the wide variety of media, which may be employed, and are not intended to be limitative.

The following are Examples of media suitable for growing strains of *Streptomyces hygroscopicus* MA-5000.

| Medium A | |
|---|---|
| Dextrose | 1.0 g. |
| Soluble starch | 10.0 g. |
| Beef extract | 3.0 g. |
| Yeast autolysate (As ardamine pH available from Yeast Products Inc., Clifton, N.J.) | 5.0 g. |
| NZ Amine-E (caesin hydrolysate-available from Humko-Sheffield-Memphis, Tenn.) | 5.0 g. |
| $MgSO_4.7H_2O$ | 0.05 g. |
| Phosphate Buffer | 2.0 ml |
| $CaCO_3$ | 0.5 g. |
| Distilled water | 1000 ml. |
| pH | 7.0–7.2 |
| Phosphate Buffer | |
| $KH_2PO_4$ | 91.0 g |
| $Na_2HPO_4$ | 95.0 g |
| Distilled water | 1000 ml |
| pH | 7.0 |
| Medium B | |
| Tomato paste | 20.0 g. |
| Primary yeast | 10.0 g. |
| Dextrin (CPC starch) | 20.0 g. |
| $CoCl_2.6H_2O$ | 0.005 g. |
| Distilled water | 1000 ml. |
| pH | 7.2–7.4 |
| Medium C | |
| Corn meal | 20.0 g. |
| Distillers solubles | 10.0 g. |
| Soybean meal | 15.0 g. |
| Sodium citrate | 4.0 g. |
| $CaCl_2.2H_2O$ | 0.5 g. |
| $MgSO_4.7H_2O$ | 0.1 g. |
| $CoCl_2.6H_2O$ | 0.01 g. |
| $FeSO_4.2H_2O$ | 0.01 g. |
| Polyglycol P2000 (Polypropylene glycol mw 2000) | 2.5 mg. |
| Distilled water | 1000 ml. |
| pH 6.5 | |
| Medium D | |
| Lactose | 20.0 g. |
| Distillers solubles | 15.0 g. |
| Autolyzed yeast (Ardamine pH) | 5.0 g. |
| Distilled water q.s. to | 1000 ml. |
| pH | 7.0 |
| Medium E | |
| Tomato paste | 40.0 g. |
| Oat flour | 10.0 g. |
| Distilled water | 1000 ml. |
| pH | 7.0 |
| Medium F | |
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard oil | 2.5 g. |
| Distilled water | 1000 ml. |
| pH | 6.7 |
| Medium G | |
| Dextrose | 10.0 g |

-continued

| | |
|---|---|
| Asparagine | 1.0 g |
| K$_2$HPO$_4$ | 0.1 g |
| MgSO$_4$.7H$_2$O | 0.5 g |
| Yeast Extract | 0.5 g |
| Oat Flour | 10.0 g |
| CaCO$_3$ | 3.0 g |
| Trace Element Mix | 10.0 ml |
| Distilled water | 1000 ml |
| Adjust pH to 7.2 | |
| Trace Element Mix | |
| FeSO$_4$.7H$_2$O | 1000 mg |
| MnSO$_4$.4H$_2$O | 1000 mg |
| CuCl$_2$.2H$_2$O | 25 mg |
| CaCl$_2$.2H$_2$O | 100 mg |
| H$_3$BO$_3$ | 56 mg |
| (NH$_4$)$_6$MO$_4$O$_{24}$.6H$_2$O | 19 mg |
| ZnSO$_4$.7H$_2$O | 200 mg |
| Distilled water | 1000 ml |
| Medium H | |
| Medium G | 1000 ml |
| Oat Flour | 10 g |
| pH | 7.2 |

The fermentation employing *Streptomyces hygroscopicus* MA-5000 can be conducted at temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Streptomyces hygroscopicus* MA-5000 loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces hygroscopicus* MA-5000. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 RPM and about 2 to 20 cubic feet per minute (CFM) of air.

The novel compound of this invention is found primarily in the mycelium on termination of the *Streptomyces hygroscopicus* MA-5000 fermentation and may be removed and separated therefrom as described below.

The separation of the novel compound from the whole fermentation broth and the recovery of said compounds is carried out by solvent extraction and application of chromatographic fractionations with various chromatographic techniques and solvent systems.

The instant compound has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antifungal activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the non-polar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compound. The use of the foregoing techniques as well as others known to those skilled in the art, will afford purified compositions containing the instant compound. The presence of the desired compound is determined by analyzing the varius chromatographic fractions for physico-chemical characteristics. The structures of the instant compound have been determined by detailed analysis of the various spectral characteristics of the compounds, in particular their nuclear magnetic resonance, mass, ultraviolet and infrared spectra.

The mass spectral data were obtained on the trimethylsilyl derivatives of the instant compounds, prepared by treatment with bis(trimethylsilyl)-trifluoroacetamide (BTSFA), 10:1 (v/v) in pyridine under nitrogen at room temperature for 18 hours to afford molecular ions in their electron impact mass spectra. Analagous silylation with perdeutero-BTSFA allowed unambiguous determination of the number of silyl groups in each molecule. High resolution exact mass measurements indicated the following molecular formulae. (The underivatized nominal molecular weights and molecular formulae have been included in the table for clarity).

| Compound | Neat Weight | Molecular Formula | Corresponding Calculated | Silyl Found | Silyl Derivative |
|---|---|---|---|---|---|
| I | 599 | C$_{29}$H$_{46}$NO$_{10}$P | 959.4836 | 959.4847 | C$_{29}$H$_{46}$NO$_{10}$P + (C$_3$H$_8$Si)$_5$ |
| II | 513 | C$_{25}$H$_{40}$NO$_8$P | 873.4468 | 873.4452 | C$_{25}$H$_{40}$NO$_8$P + (C$_3$H$_8$Si)$_5$ |
| III | 613 | C$_{30}$H$_{48}$NO$_{10}$P | 973.4992 | 973.4993 | C$_{30}$H$_{48}$NO$_{10}$P + (C$_3$H$_8$Si)$_5$ |

-continued

| Compound | Neat Weight | Molecular Formula | Corresponding Calculated | Silyl Found | Silyl Derivative |
|---|---|---|---|---|---|
| IV | 614 | $C_{30}H_{47}O_{11}P$ | 974.4832 | 974.4766 | $C_{30}H_{47}O_{11}P + (C_3H_8Si)_5$ |

Figure 1:
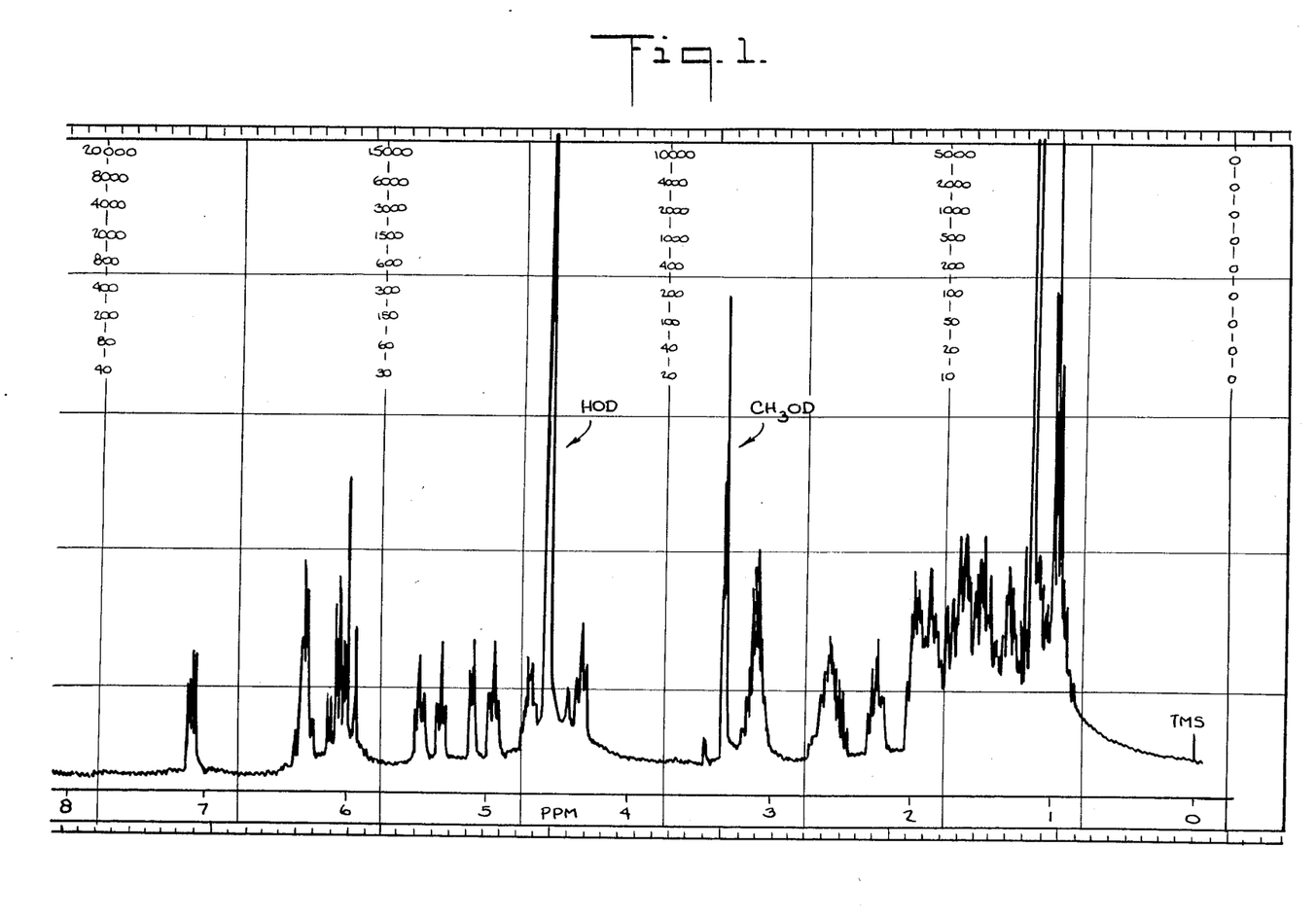
Figure 2:
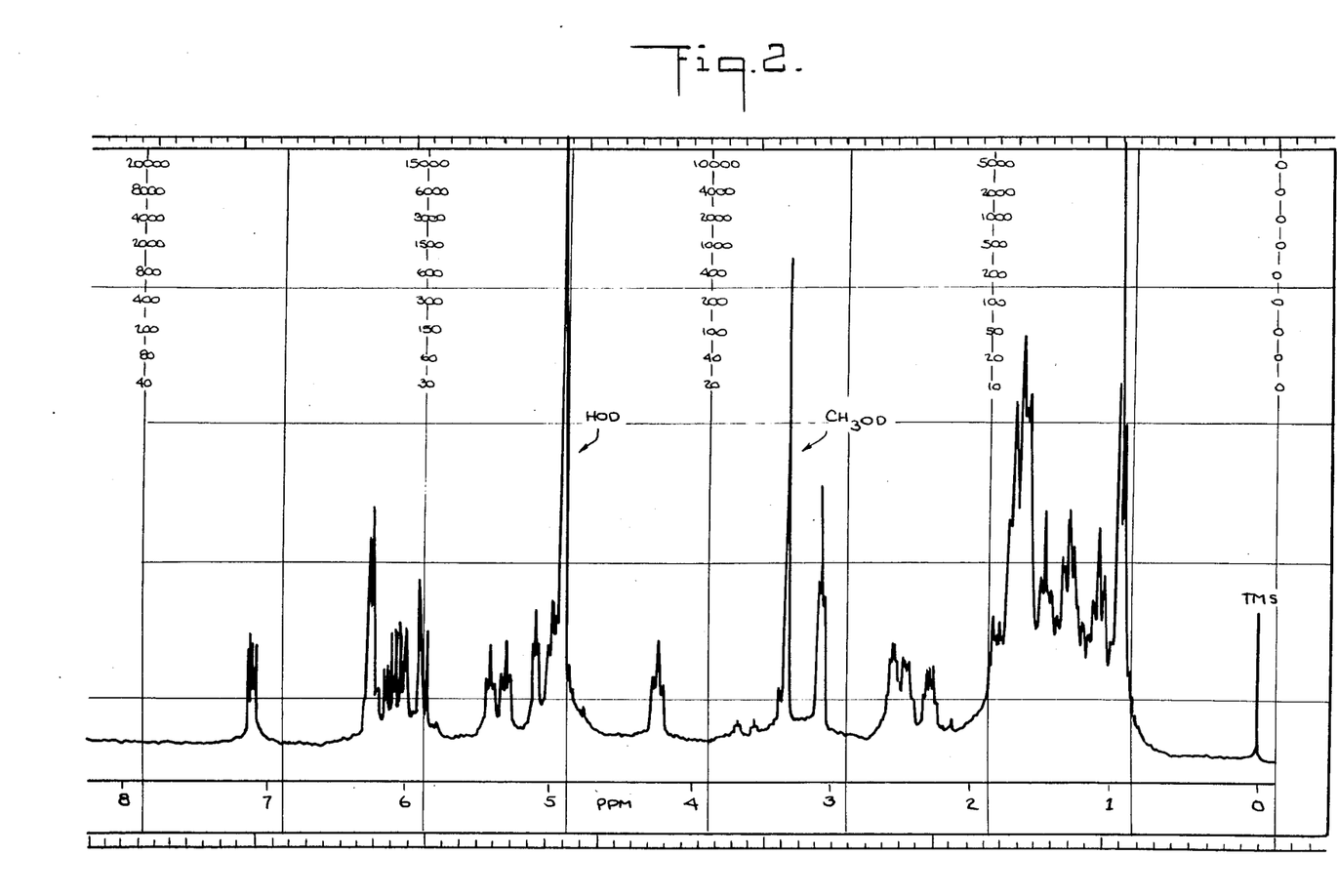
Figure 3:
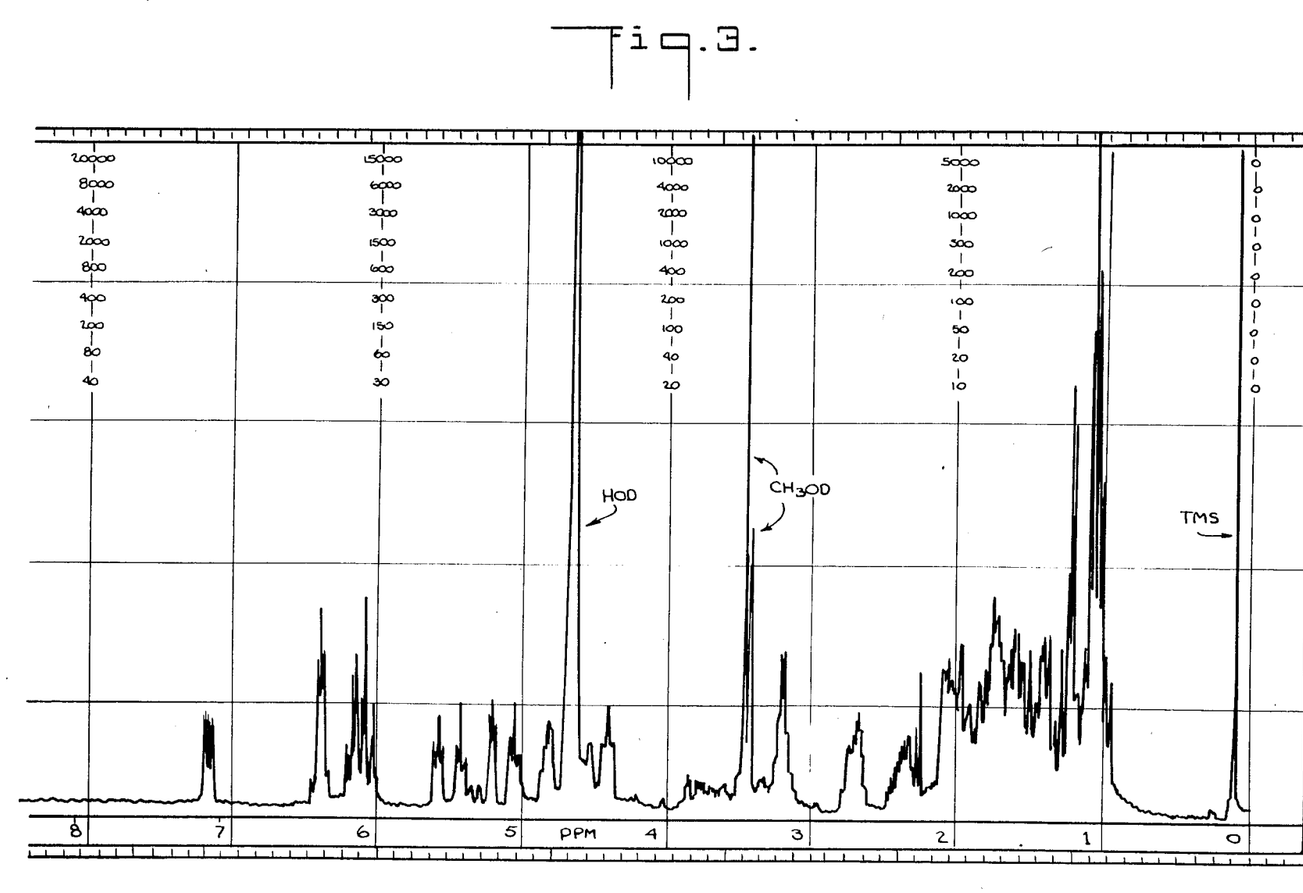
Figure 4:
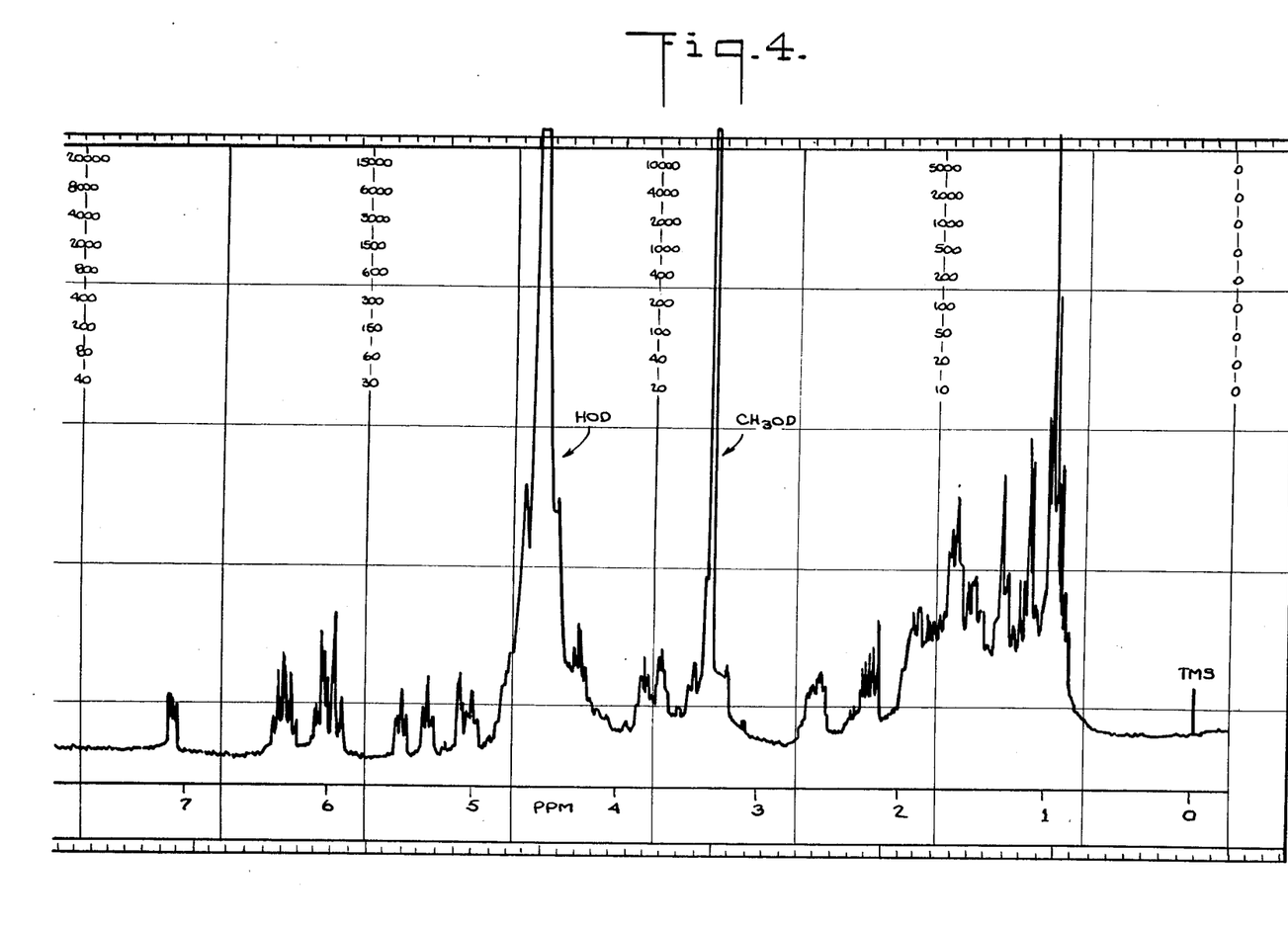

The nuclear magnetic resonance spectrum for each of Compounds I, II, III and IV are shown in attached FIGS. 1 to 4 respectively. The spectra for Compounds I, III and IV were recorded in $CD_3OD$ at 60° C. and that for Compound II in $CD_3OD$ at 25° C. A small amount of $ND_4OD$ was added to Compound II to effect complete dissolution. Chemical shifts are shown in ppm relative to internal tetramethylsilane (TMS) at 0 ppm.

Based on these experimental data, the instant compounds are believed to have the following structural formula:

wherein the compounds have the following values for $R_1$, $R_2$ and $R_3$:

| | $R_1$ | $R_2$ | $R_3$ |
|---|---|---|---|
| I | $-O-\overset{O}{\underset{\|}{C}}-\!\!\!\!<$ | $-NH_3^{\oplus}$ | $-OPO_3H^{\ominus}$ |
| II | H | $-NH_3^{\oplus}$ | $-OPO_3H^{\ominus}$ |
| III | $-O-\overset{O}{\underset{\|}{C}}-\!\!\!\!<\!\!/$ | $-NH_3^{\oplus}$ | $-OPO_3H^{\ominus}$ |
| IV | $-O-\overset{O}{\underset{\|}{C}}-\!\!\!\!<$ | $-OH$ | $-OPO_3H_2$ |

Fields of technology adversely affected by the lack of effective fungicides are many and include the paint, wood, textile, cosmetic, leather, tobacco, fur, rope, paper, pulp, plastics, fuel, rubber and food industries. Fungicides are also utilized for agricultural application, for instance in preventing or minimizing fungus growth on plants, fruits, seeds or soil.

Although many antifungal agents have been described and used heretofore in an effort to control fungi, none are entirely satisfactory and continued losses resulting from fungal attack make the problem of control a serious and lasting one. The number of fungicides practically useful in combatting fungal growth have been small and only in a few cases have synthetic organic chemicals been found applicable.

The compounds of the invention are effective in controlling the growth of Aspergillus species, for example A. niger, A. flavus, A. fumigatus, A. oryzae, A. luchensis, A. versicolor, A. sydowi, A. nidulans, A. flaucus and A. terreus, Penicillium species, for example, P. notatum, P. roqueforti, P. chrysogenum, P. oxalicum, P. spinulosum, P. martensii, P. citrinium, P. digitatum, P. expansum, P. italicum, P. cyclopium, and P. funiculosum, Neurospora series such as N. sitophila, Phoma species such as P. terrestrius, Rhizopus species, Alternaria species such as A. solani, Chaetomium species such as C. globosum, Chaetomicum species, for example, C. clivaceum, and Monilia species such as M. sitophila and M. nigra. The above fungi may be found on cosmetics, leather, electrical insulation, textiles, and numerous other materials capable of supporting their growth.

The compounds of this invention may be employed in treatment of plants, soils, fruits, seeds, fur, wood and the like. The fungicidal effectiveness of these compounds has been demonstrated against soil fungi, such as Rhizoctonia solani, Fusarium solani, and Pythium ultimum, plant fungi, for instance Erysiphe polygoni and Alternaria solani as well as against saprophytes known to attack wood, pulp and lumber such as Lenzites trabea and Ceratocystis pilifera and the fungus Pullularia pullulans which attacks paint.

In particular the compounds of this invention are useful in controlling those agricultural fungus infections that attack growing plants. The compounds are particularly effective against those fungi, which cause rice blast, tomato late blight, tomato early blight, wheat leaf rust, bean powdery mildew and tomato Fusarium wilt.

It should be understood that the compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired.

Thus it will be appreciated that compounds of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

When the active agents are employed in preventing topical fungal growth, one or more of the compounds may be uniformly distributed in a vehicle that is chemically compatible with the particular compound selected, noninhibiting with respect to the action of the antifungal and essentially non-injurious to body tissue under the conditions of use.

It should be understood that the compounds of the invention may be used in cmbination one with the other as well as with other fungicidally active materials. For instance, a mixture of the active compounds with 2-(4'-thiazolyl)benzimidazole sorbic acid or its salts, propionic acid or its salts, mycostatin, sodium diacetate, trichomycin, amphotericin, griseofulvin, undecylenic acid, chlorquinadol, 5,7-dichloro-8-hydroxyquinoline (Vioform), sodium o-phenylphenate, o-phenylphenol, biphenyl, chlorinated phenols, sodium benzoate, dehydroacetic acid and its salts or esters of parahydroxybenzoic acid, such as the methyl and propyl ester (parabens) can be used to give fungicidal effect when used in appropriate concentrations. It is quite clear, too, that the compounds defined above may be used in conjunction with effective antibacterial materials in appropriate instances so as to combine the action of each in such a situation as to be particularly useful, for instance, in applications where the presence of bacteria creates undesirable results alongside the detrimental action of fungi.

It has been found that growth of various fungi existing in soil is limited or terminated by the addition to the soil of minor quantities of the compounds described. The term soil as used herein is intended to include all media capable of supporting the growth of plants and may include humus, sand, manure, compost, artifically created plant growth solution, and the like.

We have also found that the fungicides of the invention are effective against fungal diseases of plants, and may be effectively used either by direct contact with the foliage or systemically, by introduction through the roots.

The following examples are being provided in order that the instant invention may be more fully understood. Such examples are not to be construed as being limitative of the invention.

EXAMPLE 1

1. "A" Stage:

Culture MA5000 is maintained in the lyophilized state in a 1.0 ml ampule containing 0.15 ml of a skim milk suspension of the culture.

2. "B" Stage:

Vessel: 250 ml 3 baffled Erlenmeyer flask containing 50 ml medium per flask.

| Medium: | Wt/Vol |
|---|---|
| Dextrose | 0.1% |
| Soluble Starch | 1.0% |
| Beef Extract | 0.3% |
| Ardamine pH | 0.5% |
| NZ-Amine Type E | 0.5% |
| $MgSO_4.7H_2O$ | 0.005% |
| 1.34 M Phosphate Buffer | 0.02% Vol/Vol |
| $CaCO_3$ (after pH adjustment) | 0.05% |
| Phosphate Buffer | |
| $KH_2PO_4$ | 9.1% |
| $Na_2HPO_4$ | 9.5% |

Inoculum: Contents of one lyophilization tube into each "B" flask

Incubation: 48 hours at 28° C. on a rotary shaker with a 2″ throw rotating at 220 RPM.

Sterility: Streak plates and gram stain

3. "C" Stage:

Vessel: 2-liter 3 baffled Erlenmeyer flask containing 500 ml medium

Medium: Same as "B" Stage
Inoculum: 10 ml from "B" Stage
Incubation: Same as "B" Stage
Sterility: Same as "B" Stage 4. "D" Stage:

Vessel: 189-liter stainless steel fermentor containing 160 liters of medium

| Medium: | |
|---|---|
| Dextrose (Cerelose) | 160 gms |
| Starch Modfied CPC | 1600 gms |
| Meat Extract | 480 gms |
| Ardamine pH | 800 gms |
| NZ Amine Type E | 800 gms |

| -continued | |
|---|---|
| Medium: | |
| $MgSO_4.7H_2O$ | 8 gms |
| $KH_2PO_4$ | 29 gms |
| $Na_2HPO_4$ | 30 gms |
| pH to | 7.0–7.2 |
| Add $CaCO_3$ | 80 gms |

Sterilization: 121° C. for 15 minutes
Inoculum: 500 ml from "C" Stage
Incubation:
(a) Temp: 28° C.
(b) Airflow: 3 ft³/min
(c) Agitation: 150 RPM
(d) Pressure: 30 psig
(e) Cycle: 48 hrs
Defoamer: Polyglycol 2000
Sterility: Microscopic examination and YED streak plates at 28° C. and 37° C.

5. "E" Stage:

Vessel: 756-liter fermentor containing 467 liters of medium

| Medium: | Fermentation 1 | Fermentation 2 |
|---|---|---|
| Corn Meal | 9340 gms | 9680 gms |
| Distillers Solubles | 4670 gms | 4840 gms |
| Soybean Meal | 7005 gms | 7260 gms |
| $CaCl_2.2H_2O$ | 233.5 gms | 242 gms |
| $MgSO_4.7H_2O$ | 46.7 gms | 48.4 gms |
| $CoCl_2.6H_2O$ | 4.7 gms | 4.8 gms |
| $FeSO_4.7H_2O$ | 4.7 gms | 4.8 gms |
| $CaCO_3$ | 1868 gms | 1936 gms |
| Polyglycol P-2000 | 116 ml | 1.2 l |
| pH to | 6.5 | 6.5 |
| Volume | 467 liters | 484 liters |

Sterilization: 121° C. for 15 minutes
Inoculum: 43 liters from "D" Stage
Incubation:
(a) Temp: 28° C.
(b) Airflow: 10 ft³/min
(c) Agitation: 130 RPM
(d) Pressure: 13 psig
(e) Cycle: 3 days
Defoamer: Polyglycol P-2000
Sterility: Microscopic examination and YED streak plates at 28° C. and 37° C.
Harvest: Into drums for work-up as in Examples 2 and 3

EXAMPLE 2

Four hundred liters of whole broth from Example 1 "E" Stage fermentation 1, were filtered through a press after the addition of celite, a filter aid. The mycelial cake was extracted with 32 liters of 50% aqueous acetone for one hour. This slurry was filtered and the extract concentrated in vacuo to an aqueous solution. This concentrate was added to the filtered broth and the entire solution was extracted twice with a half volume of methylene chloride. The aqueous phase was then passed through 40 liters Dowex 1X2 ($Cl^-$) column. After a water wash the column was eluted with 120 liters of 5% sodium chloride followed by 120 liters of 3% ammonium chloride in 90% methanol. The second eluate was concentrated in vacuo to 4 liters and eluted to 16 liters with water. This solution was passed through a 16 liter Amberlite XAD-2 column. After a water wash the column was eluted with 48 liters 10% aqueous acetone, 48 liters 20% aqueous acetone and 50% aqueous acetone. The third eluate was concentrated to an aqueous solution of 4 liters which was extracted twice with 8.8 liters butanol. The butanol extracts were concentrated to a small volume and the activity precipitated with the addition of hexane. The precipitate was chromatographed on a 500 ml Mallinkrodt CC-7 silica gel column in acetone with stepwise increases of methanol in acetone. Active cuts were combined and chromatographed on a 225 ml LH-20 column in methanol. Active cuts were combined and rechromatographed on the same column in 25% acetone/methanol yielding 549 mg. Aliquots of this purified preparation were chromatographed on a preparative RP-2, 10 μm HPLC column (9 mm×30 cm) using a methanol—1% HoAc gradient system. Fractions of the three separated components were combined, concentrated to aqueous solutions and freeze-dried to yield the following samples:

Component I: 18 mg
Component II: 16 mg
Component III: 14 mg

The remainder of the LH-20 rich cut was chromatographed on a preparative RP-18, 10 μm HPLC column (9 mm×30 cm) using the isocratic system 500/450/50 methanol/water/1.0M PO4 pH 6.5 to yield the following samples:

Component I: 15.8 mg
Component II: 9.9 mg

EXAMPLE 2

The fermentation of Example 1 using "E" Stage fermentation 2 was carried out twice and each 400 liter fermentation was filtered 320 liters through a press after addition of celite. Each mycelial cake was extracted with 320 liters of 50% aqueous acetone for one hour. The acetone extracts were filtered and concentrated to aqueous solutions. These extracts and the filtrates were individually extracted with a half volume of methylene chloride and then each extracted twice with a half volume of butanol. The butanol extracts were combined and evaporated onto 8 liters Grace silica gel. The coated gel was eluted sequentially with ethyl acetate, acetone, 10% methanol/acetone and 100% methanol. The methanol eluate was concentrated (180 gm) onto 700 ml Baker silica gel and placed on top of a two-liter silica gel column. This column was eluted with acetone, then stepwise with 20-40-75% methanol/acetone. The active cuts were concentrated, extracted with butanol (16 gm) and chromatographed on a two-liter EM 25-40 μm RP C-18 column with isocratic elution of 60/40 methanol/0.01M PO4pH 6.5. Cuts were combined based on their zone size and analytical HPLC analysis and rechromatographed on a 200 ml EM 25-40 μm RP C-18 column using 55/45 methanol/buffer. Final purification of the individual active components was achieved by chromatography on a 10 μm RP C-18 column, 9 mm×50 cm.

Component II: 40 mg
Component III: 6.7 mg
Component IV: 2.5 mg

What is claimed is:

1. A compound having the formula:

wherein the compounds have the following values for $R_1$, $R_2$ and $R_3$:

| | $R_1$ | $R_2$ | $R_3$ |
|---|---|---|---|
| I | −O−C(=O)−⟨ | $-NH_3^{\oplus}$ | $-O-PO_3H^{\ominus}$ |
| II | H | $-NH_3^{\oplus}$ | $-O-PO_3H^{\ominus}$ |
| III | −O−C(=O)−⟨ | $-NH_3^{\oplus}$ | $-O-PO_3H^{\ominus}$ |
| IV | −O−C(=O)−⟨ | $-OH$ | $-O-PO_3H_2$ |

2. The compound of claim 1 wherein $R_1$ is $R_2$ is $-NH_3^{\oplus}$ and $R_3$ is $-O-PO_3H^{\ominus}$.

3. The compound of claim 1 wherein $R_1$ is H, $R_2$ is $-NH_3^{\oplus}$ and $R_3$ is $-O-PO_3H^{\ominus}$.

4. The compound of claim 1 wherein $R_1$ is $R_2$ is $-NH_3^{\oplus}$ and $R_3$ is $-O-PO_3H^{\ominus}$.

5. The compound of claim 1 wherein $R_1$ is $R_2$ is $-OH$ and $R_3$ is $-O-PO_3H_2$.

6. An antifungal composition which comprises one or more compounds of claim 1 and a pharmaceutically acceptable carrier.

7. A method for the treatment of fungus infections which comprises treating an area infected with fungi with one or more compounds of claim 1.

* * * * *